US012106956B2

(12) United States Patent
Edquist et al.

(10) Patent No.: US 12,106,956 B2
(45) Date of Patent: Oct. 1, 2024

(54) COLOR MIXED EXCIMER LAMP FOR SOFT GLOW EFFECT

(71) Applicant: B/E AEROSPACE, INC., Winston Salem, NC (US)

(72) Inventors: John D. Edquist, Milwaukee, WI (US); Jeremy John Fredrich, West Allis, WI (US)

(73) Assignee: B/E AEROSPACE, INC., Winston Salem, NC (US)

(*) Notice: Subject to any disclaimer, the term of this patent is extended or adjusted under 35 U.S.C. 154(b) by 338 days.

(21) Appl. No.: 17/736,358

(22) Filed: May 4, 2022

(65) Prior Publication Data

US 2022/0375741 A1    Nov. 24, 2022

Related U.S. Application Data

(60) Provisional application No. 63/189,951, filed on May 18, 2021.

(51) Int. Cl.
| | |
|---|---|
| *A61L 2/10* | (2006.01) |
| *A61L 9/20* | (2006.01) |
| *H01J 65/04* | (2006.01) |

(52) U.S. Cl.
CPC .............. *H01J 65/046* (2013.01); *A61L 2/10* (2013.01); *A61L 9/20* (2013.01); *A61L 2202/11* (2013.01); *A61L 2202/16* (2013.01); *A61L 2202/25* (2013.01)

(58) Field of Classification Search
CPC .. H01J 65/046; A61L 2/10; A61L 9/20; A61L 2202/11; A61L 2202/16; A61L 2202/25; B64D 47/02; F21S 8/02; F21V 3/049; F21V 33/0064; F21Y 2113/10; F21Y 2113/20

USPC ..................................... 250/504 R
See application file for complete search history.

(56) References Cited

U.S. PATENT DOCUMENTS

| | | | |
|---|---|---|---|
| 6,211,383 B1 * | 4/2001 | MacDonald ........... | B43M 11/08 548/479 |
| 10,655,818 B2 | 5/2020 | Callahan | |
| 11,006,493 B1 | 5/2021 | Meir et al. | |

(Continued)

FOREIGN PATENT DOCUMENTS

| | | |
|---|---|---|
| DE | 202020001197 | 4/2020 |
| WO | 2020121934 | 6/2020 |

OTHER PUBLICATIONS

European Patent Office, European Search Report dated Oct. 14, 2022 in Application No. 22174109.3.

*Primary Examiner* — Jason L McCormack
(74) *Attorney, Agent, or Firm* — SNELL & WILMER L.L.P.

(57) ABSTRACT

A system for improving an appearance of light from an excimer lamp includes the excimer lamp configured to output excimer light that includes ultraviolet light having an ultraviolet wavelength and visible light having a first visible wavelength or spectra. The system further includes at least one additional light source configured to be packaged with the excimer lamp and to output additional light having a second visible wavelength or spectra. The system further includes a cover that is at least one of transparent or translucent to the ultraviolet wavelength and having a surface pattern that causes the excimer light to blend with the additional light.

20 Claims, 10 Drawing Sheets

(56) References Cited

U.S. PATENT DOCUMENTS

| | | | |
|---|---|---|---|
| 2005/0088098 A1* | 4/2005 | Reich | H01J 61/35 |
| | | | 313/493 |
| 2007/0045641 A1 | 3/2007 | Chua et al. | |
| 2007/0053188 A1 | 3/2007 | New et al. | |
| 2016/0316527 A1* | 10/2016 | Allen | H05B 47/16 |
| 2018/0209609 A1* | 7/2018 | Hikmet | F21V 9/06 |
| 2020/0038542 A1 | 2/2020 | Franklin et al. | |
| 2020/0215214 A1 | 7/2020 | Rosen et al. | |
| 2021/0030905 A1* | 2/2021 | Barron | A61L 2/085 |
| 2021/0369905 A1* | 12/2021 | Bosua | H05B 47/105 |

* cited by examiner

COLOR MIXED EXCIMER LAMP FOR SOFT GLOW EFFECT

CROSS REFERENCE TO RELATED APPLICATIONS

This application claims priority to, and the benefit of, U.S. Provisional Patent Application Ser. No. 63/189,951, entitled "COLOR MIXED EXCIMER LAMP FOR SOFT GLOW EFFECT," filed on May 18, 2021. The '951 Application is hereby incorporated by reference in its entirety for all purposes.

FIELD

The present disclosure relates to systems and methods for improving an appearance of light generated by an excimer lamp that outputs ultraviolet light.

BACKGROUND

Ultraviolet (UV) light has been found to be an effective disinfectant. Of the various UV wavelengths, 222 nanometers (222 nm) has been found to be particularly promising (effective and safe for humans in moderate doses). Currently, UV lights that emit light of this wavelength are primarily available as gas-discharge excimer lamps. When active, these lamps output UV light having this desirable wavelength, but also output visible light that is viewed as a purple color to a human eye. The visible light also may appear as a plasma arc. Evidence supports the fact that this UV light is safe in occupied spaces, but a person unfamiliar with the technology may be concerned by the appearance of the visible light. Furthermore, it is also desirable to hide the excimer lamps from view in response to them being turned off.

SUMMARY

Disclosed herein is a system for improving an appearance of light from an excimer lamp. The system includes the excimer lamp configured to output excimer light that includes ultraviolet light having an ultraviolet wavelength and visible light having a first visible wavelength or spectra. The system further includes at least one additional light source configured to be packaged with the excimer lamp and to output additional light having a second visible wavelength or spectra. The system further includes a cover that is at least one of transparent or translucent to the ultraviolet wavelength and having a surface pattern that causes the excimer light to blend with the additional light.

In any of the foregoing embodiments, the ultraviolet wavelength of the ultraviolet light that is output by the excimer lamp is between 200 and 225 nanometers.

In any of the foregoing embodiments, the excimer lamp includes a plurality of excimer lamps spaced apart, and the at least one additional light source includes a plurality of additional light sources interspersed with the plurality of excimer lamps.

In any of the foregoing embodiments, a combination of the excimer light and the additional light appears white to a human eye.

In any of the foregoing embodiments, the second visible wavelength or spectra is selected to cause a combination of the visible light having the first visible wavelength or spectra and the additional light having the second visible wavelength or spectra to appear white to a human eye.

In any of the foregoing embodiments, the at least one additional light source includes at least two additional light sources that each output the additional light having a different visible wavelength such that a combination of the additional light that is output by the at least two additional light sources appears white to a human eye.

In any of the foregoing embodiments, a second luminescence of the additional light is at least one order of magnitude greater than a first luminesce of the visible light that is output by the excimer lamp so as to mask the visible light that is output by the excimer lamp.

In any of the foregoing embodiments, the cover includes a quartz glass.

In any of the foregoing embodiments, the quartz glass is etched to have the surface pattern.

Also disclosed is a system for improving an appearance of light from an excimer lamp. The system includes the excimer lamp configured to output excimer light that includes ultraviolet light having an ultraviolet wavelength and visible light having a first visible wavelength or spectra. The system further includes at least one additional light source configured to be packaged with the excimer lamp and to output additional light having a second visible wavelength or spectra. The system further includes a casing having an outlet. The system further includes a first reflector configured to reflect the excimer light and the additional light towards the outlet. The system further includes a second reflector configured to reflect the excimer light and the additional light from the first reflector, from the excimer lamp, and from the at least one additional light source out of the outlet, the second reflector configured to reflect the ultraviolet light.

In any of the foregoing embodiments, the second reflector has a polytetrafluoroethylene (PTFE) coating.

In any of the foregoing embodiments, the excimer lamp and the casing each have an elongated shape, and the at least one additional light source includes an array of light sources spaced along a length of the casing.

In any of the foregoing embodiments, the ultraviolet wavelength of the ultraviolet light that is output by the excimer lamp is between 200 and 225 nanometers.

In any of the foregoing embodiments, a combination of the excimer light and the additional light appears white to a human eye.

In any of the foregoing embodiments, the second visible wavelength or spectra is selected to cause a combination of the visible light having the first visible wavelength or spectra and the additional light having the second visible wavelength or spectra to appear white to a human eye.

In any of the foregoing embodiments, the at least one additional light source includes at least two additional light sources that each output the additional light having a different visible wavelength such that a combination of the additional light that is output by the at least two additional light sources appears white to a human eye.

In any of the foregoing embodiments, a second luminescence of the additional light is at least one order of magnitude greater than a first luminesce of the visible light that is output by the excimer lamp so as to mask the visible light that is output by the excimer lamp.

Also disclosed is a method for improving an appearance of light from an excimer lamp. The method includes outputting, by the excimer lamp, excimer light that includes ultraviolet light having an ultraviolet wavelength and visible light having a first visible wavelength or spectra. The method further includes outputting, by at least one additional light source, additional light having a second visible wavelength or spectra. The method further includes blending the excimer light with the additional light to hide the visible light having the first visible wavelength or spectra that is output by the excimer lamp.

In any of the foregoing embodiments, blending the excimer light with the additional light includes diffusing, by a quartz glass cover, the excimer light and the additional light.

In any of the foregoing embodiments, blending the excimer light with the additional light includes blending, using at least one reflector configured to reflect the excimer light, the excimer light and the additional light prior to a combination of the excimer light and the additional light leaving an outlet.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the exemplary embodiments of the disclosure, it should be understood that other embodiments may be realized and that logical changes and adaptations in design and construction may be made in accordance with this disclosure and the teachings herein. Thus, the detailed description herein is presented for purposes of illustration only and not limitation. The steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

Figure 1A:
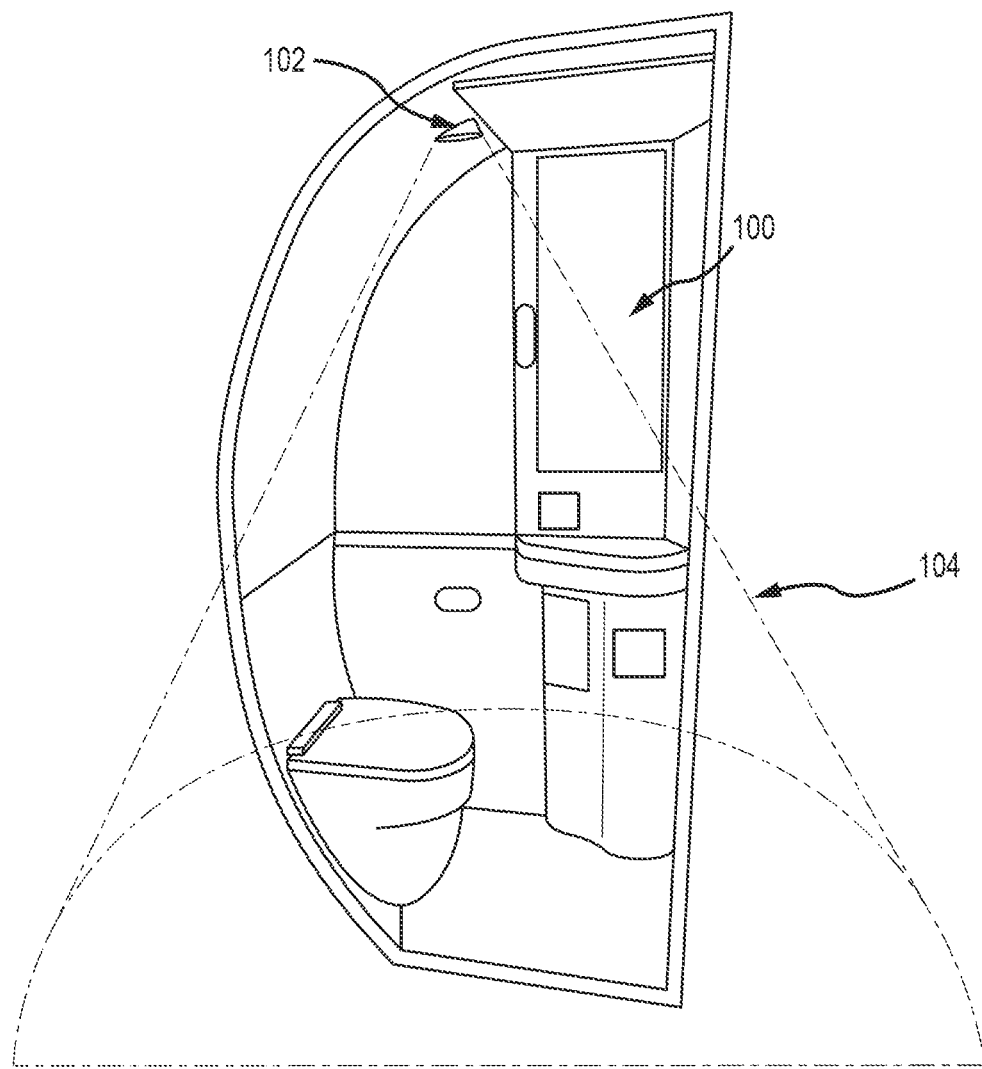
FIG. 1A illustrates an aircraft lavatory having a system for improving an appearance of light from an excimer lamp, in accordance with various embodiments.

Referring now to FIG. 1A, a portion of an aircraft lavatory 100 is shown. The lavatory 100 includes a system 102, or light source 102, that outputs a combination of light 104 that includes ultraviolet (UV) light and visible light. Where used herein, UV light may refer to light that is visible to living eyes or invisible to living eyes. In that regard, the phrase "UV light" may be replaced with "UV radiation." The UV light may have a wavelength that is designed to injure or kill pathogens. For example, the wavelength may be between 200 and 225 nanometers (0.0079 thousandths of an inch, or mils, and 0.0088 mils), between 220 and 225 nanometers (0.0087 mils and 0.0088 mils), or about 222 nanometers (0.0087 mils). Where used in this context, about refers to the referenced value plus or minus 2 percent of the referenced value. The light 104 from the system 102 may be directed towards a portion of the lavatory 100 for which disinfecting is desirable.

Figure 1B:
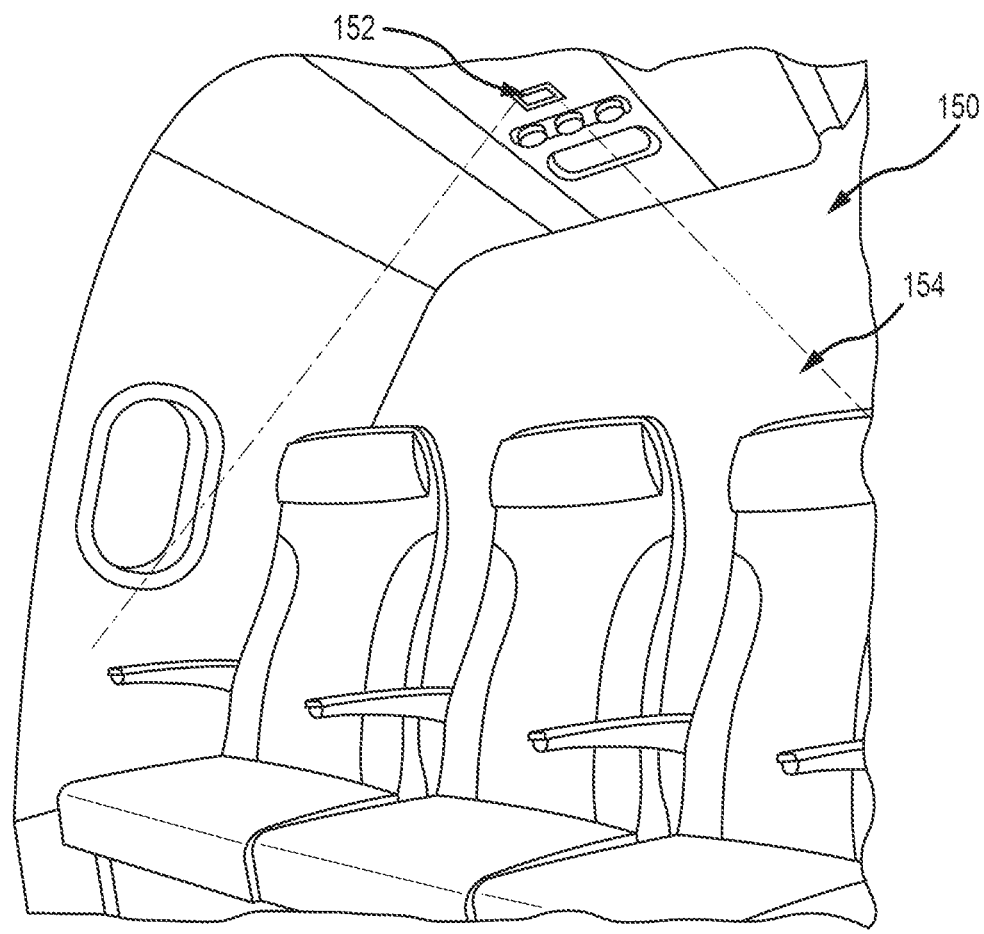
FIG. 1B illustrates a portion of an aircraft cabin having a system for improving an appearance of light from an excimer lamp, in accordance with various embodiments.

Referring now to FIG. 1B, a portion of an aircraft cabin 150 is shown. The cabin 150 may include a system 152, or light source 152, that outputs a combination of UV and visible light 154. The system 152 and light 154 may be similar to the system 102 and light 104 of FIG. 1A.

Figure 2:
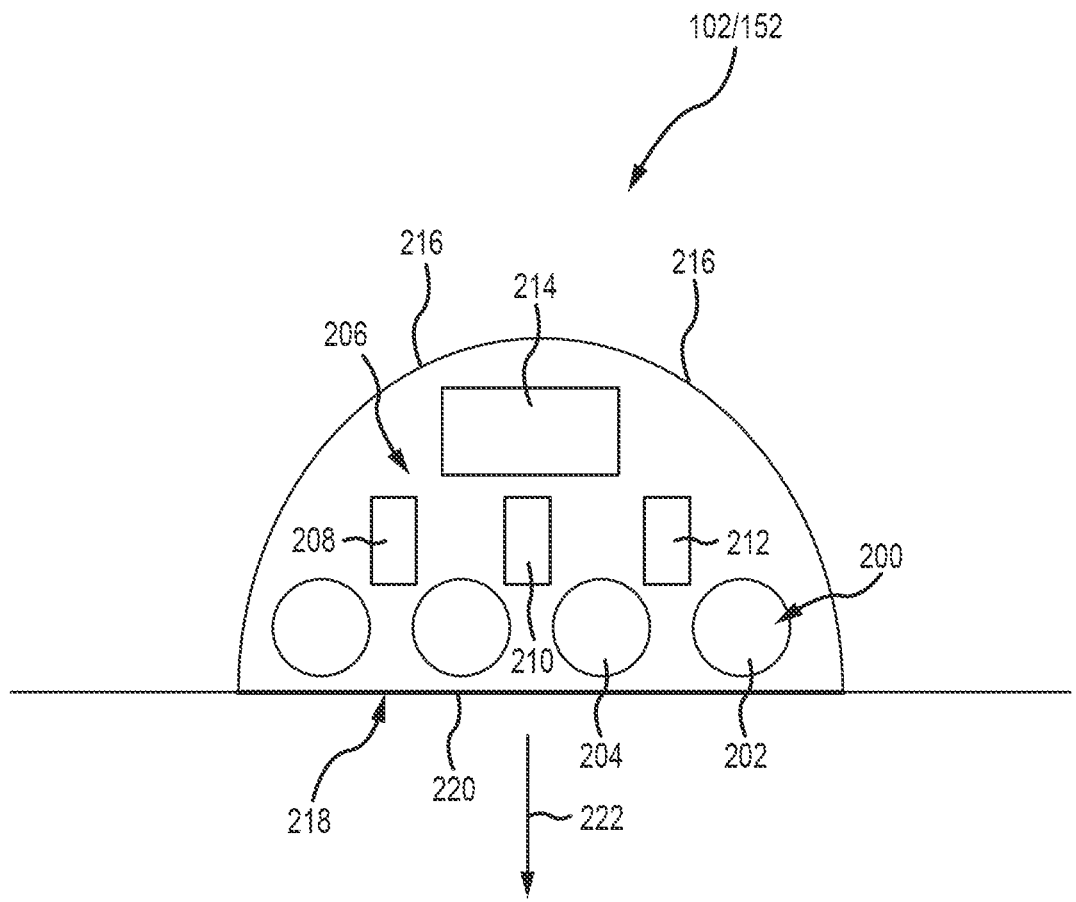
FIG. 2 illustrates various features of the system of FIG. 1A, in accordance with various embodiments.

Turning to FIG. 2, additional details of the system 102 or system 152 of FIG. 1A or FIG. 1B is shown. In particular, the system 102 may include at least one excimer lamp 200, at least one additional light source 206, a casing 216, and a cover 220.

The excimer lamp 200 may include one or multiple excimer lamp elements. As shown, the at least one excimer lamp 200 includes four excimer lamp elements, including a first excimer lamp element 202 and a second excimer lamp element 204, which may be spaced apart. The excimer lamp 200 is designed to output excimer light which includes UV light having a wavelength that injures or kills pathogens (i.e., which disinfects, such as 222 nanometers) and further includes visible light as a byproduct. The visible light that is output by the excimer lamp 200 may have an undesirable color, may undesirably appear as arcing, or may have other undesirable properties.

It is desirable to mask, occlude, or otherwise hide the visible light that is generated by the excimer lamp 200 while still achieving the disinfecting effect of the UV light from the excimer lamp 200. In that regard, the at least one additional light source 206 may generate additional visible light that mixes with the visible light from the excimer lamp 200 to appear white or another desirable color, or to otherwise mask the light from the excimer lamp 200.

Figure 6A:
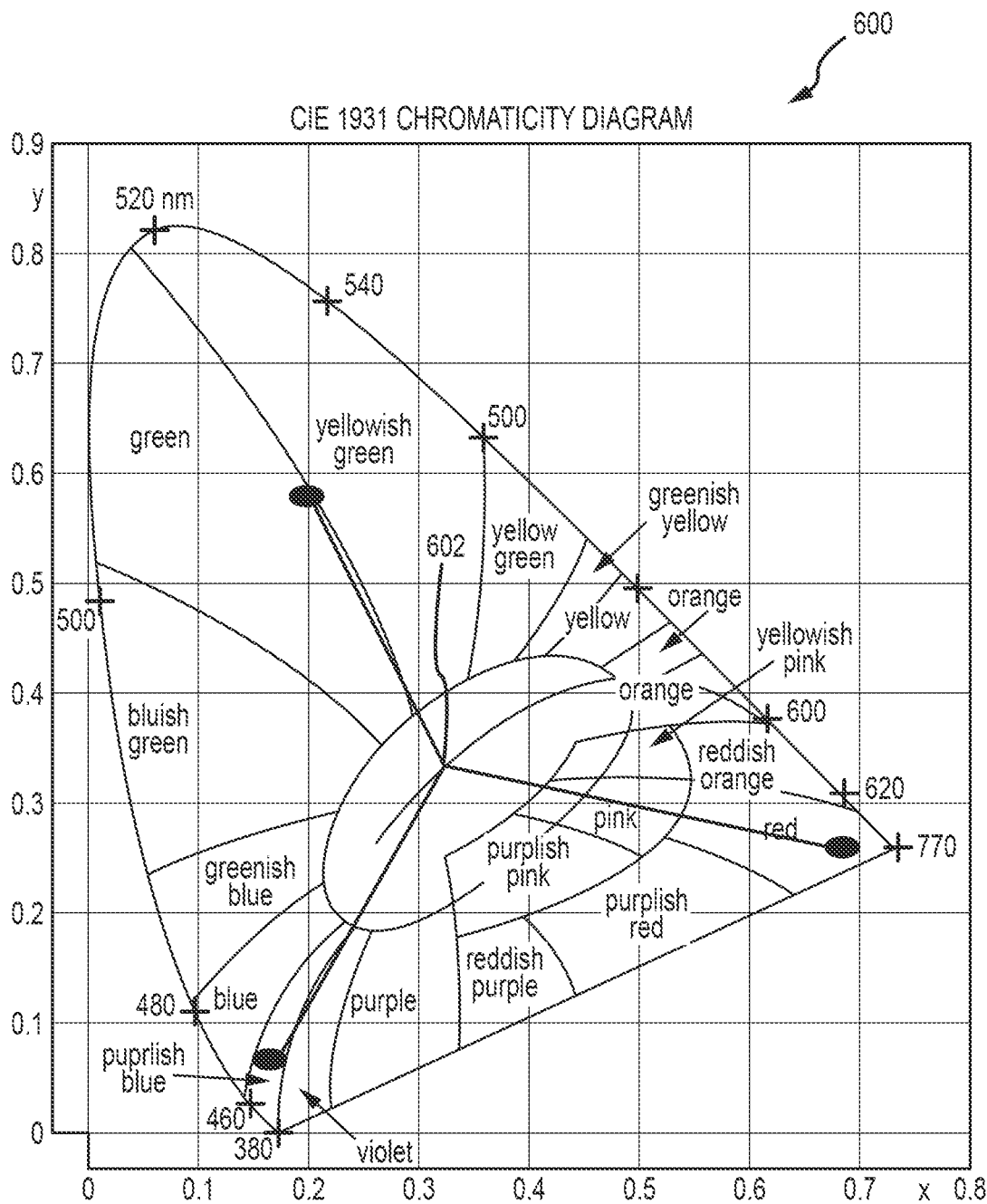
FIG. 6A illustrates a chromaticity diagram, in accordance with various embodiments.
Figure 6B:
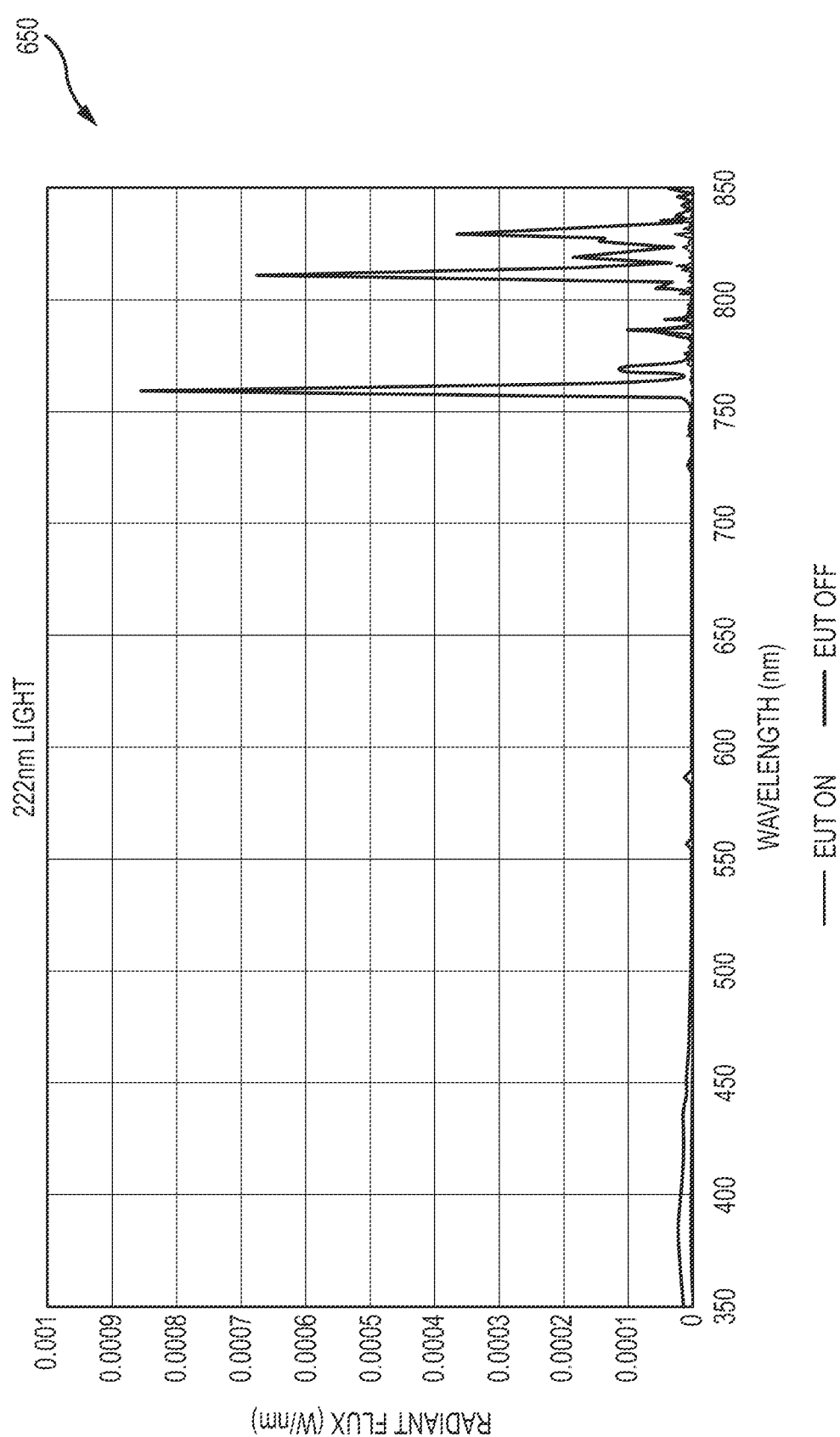
FIG. 6B illustrates a chart showing wavelengths of visible light that are generated by an ultraviolet excimer lamp, in accordance with various embodiments.

For example, and referring briefly to FIGS. 6A and 6B, a chart illustrates the visible light that is output by 222 nanometer excimer lamps. As shown, the visible light includes peaks around 400 nanometers (0.016 mils, which corresponds to a blue color) as well as peaks between 750 and 850 nanometers (0.030 mils and 0.033 mils, which corresponds to a red color). A chromaticity diagram 600 of FIG. 6A illustrates the various wavelengths and corresponding colors. In order to achieve a white color, an average of all wavelengths of light that will be mixed should be relatively close to a center 602 of the diagram 600. Thus, one way to achieve mask the visible light from an excimer lamp as white light is to combine a green or yellow-green color with the purple and red colors of visible light that is output by the excimer lamp.

Returning reference to FIG. 2, the at least one additional light source 206 may thus include one or more light source (e.g., first light source 208, second light source 210, and/or third light source 212) that each outputs light having a green or yellow-green color such that the visible light from the excimer lamp 200 and the at least one additional light source 206 appears white. The wavelength of the light that is output by the one or more light source 206 may also combine with the visible light of the excimer lamp to generate any other desirable color such as blue, green, or other lighting.

Another way to mask the visible light from the excimer lamp 200 is to overpower the visible light from the excimer lamp by causing the at least one additional light source 206 to have a luminescence that is significantly greater, such as one or more order of magnitude greater, than a luminescence of the visible light that is output by the excimer lamp 200. For example, the at least one additional light source 206 may include a white light source 214 that generates white visible light and has a luminescence that is significantly greater than the visible light that is output by the excimer lamp 200.

In various embodiments, the at least one additional light source 206 may include a plurality of light sources including a first light source 208, a second light source 210, and a third light source 212. The first, second, and third light sources 208, 210, 212 may each output visible light having a different wavelength. For example, the color of light that is output by the first light source 208 may be red, the color of light that is output by the second light source 210 may be green, and the color of light that is output by the third light source 212 may be blue. The light from the first, second, and third light sources 208, 210, 212 may mix with the visible light from the excimer lamp 200 to result in a white color. In various embodiments, the intensity or other property of the light generated by the light sources 206 may be adjustable such that the system 102 may be designed to output light of multiple colors. For example, during certain times, the system 102 may be controlled to output white light, and at other times (e.g., when it is desirable for passengers to sleep), the system 102 may be controlled to output blue light, which is known to be soothing. As another example, during daytime the system 102 may be controlled to output light having a color temperature of 4,000 Kelvin, and during nighttime the system 102 may be controlled to output light having a color temperature of 2,700 Kelvin.

In embodiments in which the excimer lamp 200 includes a plurality of excimer lamps, the additional light sources 208, 210, 212 may be interspersed with the plurality of excimer lamps. That is, each additional light source 208, 210, 212 may be located between one or more of the excimer lamps (e.g., the third light source 212 may be located between the first and second excimer lamp elements 202, 204).

The system 102 may further include a casing 216 having an outlet 218. The casing 216 may be formed from any material and may define a chamber. The excimer lamp 200 and the at least one additional light source 206 may each be housed in the chamber within the casing 216. That is, the additional light source 206 may be packaged with the excimer lamp 200. Combined light from the additional light source 206 and the excimer lamp 200 may be output via the outlet 218, as shown by an arrow 222.

The system 102 may further include a cover 220 which covers the outlet 218. The cover 220 may be at least one of transparent or translucent to the UV light from the excimer lamp 200 as well as to the combination of visible light from the excimer lamp 200 and the at least one additional light source 206. For example, the cover 220 may include a quartz glass and/or a sapphire crystal. In addition, the cover 220 may have a surface pattern that facilitates diffusion of the combined light from the excimer lamp 200 and the at least one additional light source 206. For example, the surface pattern may be etched or otherwise formed into the material of the cover 220. This surface pattern (e.g., via the etching) may be formed in such a way as to diffuse the light from the excimer lamp 200 and from the at least one additional light source 206 to give the appearance of an opaque lens.

Figure 3:
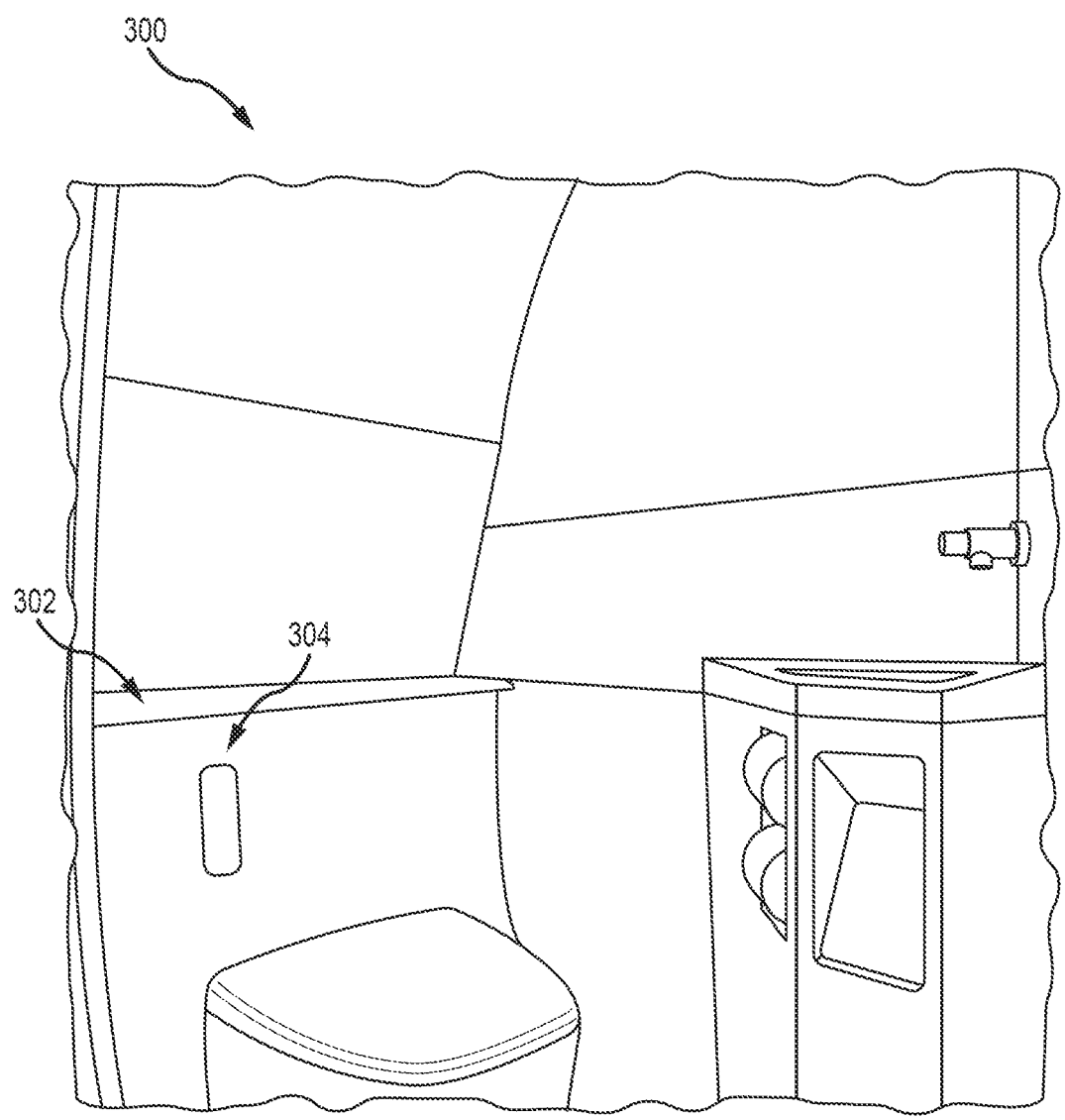
FIG. 3 illustrates a portion of an aircraft lavatory having a system for improving an appearance of light from an excimer lamp, in accordance with various embodiments.

Referring now to FIG. 3, a portion of an aircraft lavatory 300 is shown. The lavatory 300 may include an elongated system 302, or light source 302, that outputs a combination of UV and visible light 304. The system 302 and light 304 may be similar to the system 102 and light 104 of FIG. 1A except for the elongated shape of the system 302.

Figure 4A:
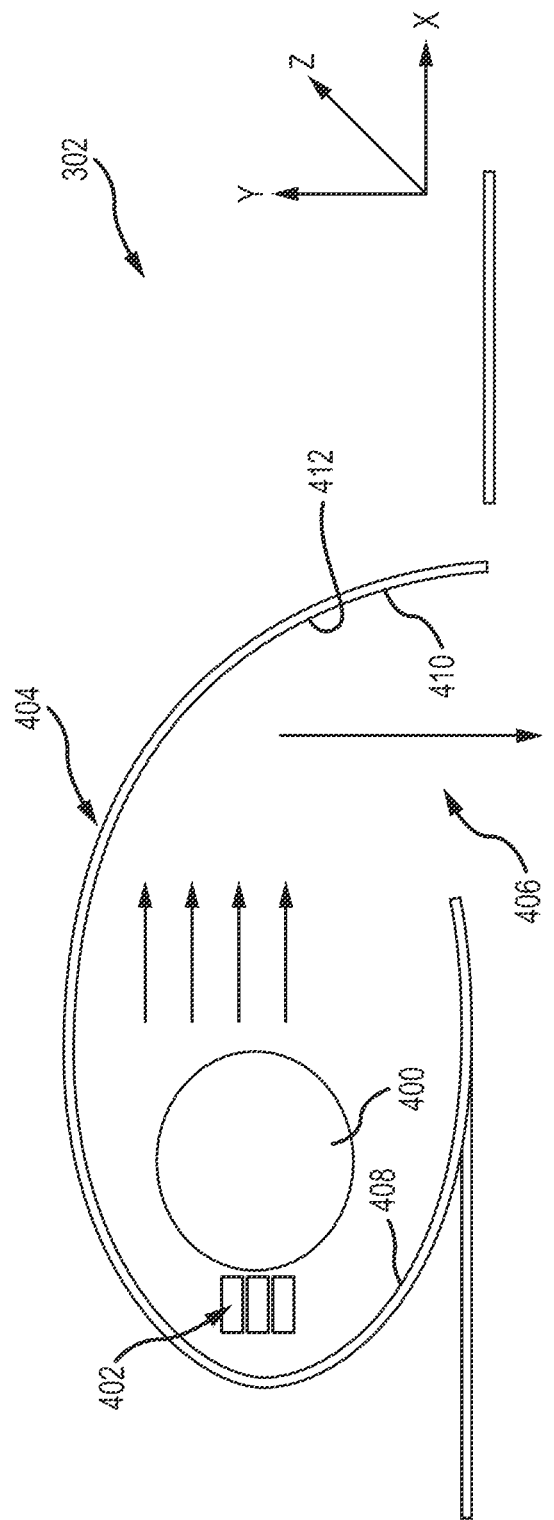
FIG. 4A illustrates various features of the system of FIG. 3, in accordance with various embodiments.
Figure 4B:
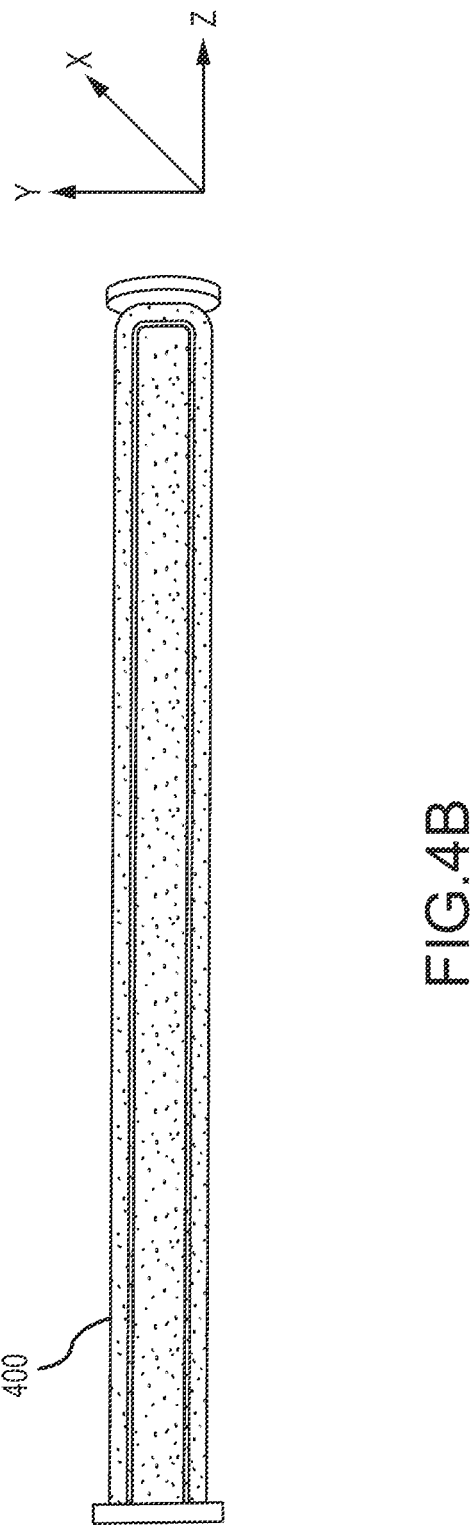
FIG. 4B illustrates an elongated excimer lamp of the system of FIG. 3, in accordance with various embodiments.

Referring to FIGS. 3, 4A, and 4B, an X-Y-Z axis is shown to illustrate the relative locations of the various elements.

In particular, the system 302 may include an elongated excimer lamp 400. The excimer lamp 400 may have a longitudinal axis that extends along the X-axis. The excimer lamp 400 may generate or output similar excimer light as the excimer lamp 200 of FIG. 2. In particular the excimer lamp 400 may output disinfecting UV light along with visible light. As with the excimer lamp 200 of FIG. 2, it may be desirable to mask or otherwise hide the visible light generated by the excimer lamp 200. The elongated shape of the excimer lamp 400 allows for an elongated stream of light 304 to disinfect a relatively large surface.

The system 302 may further include at least one additional light source 402 that outputs additional light in the visible spectrum. The at least one additional light source 402 may be designed such that a combination of the excimer light from the excimer lamp and the additional light from the additional light source appears white or another desirable color.

The at least one additional light source 402 may have any of the properties as the at least one additional light source 206 of FIG. 2. For example, the at least one additional light source 402 may output light having a single wavelength that combines with the visible light from the excimer lamp 400 to appear white. As another example, the at least one additional light source 402 may have an intensity that is significantly greater than an intensity of the excimer lamp 400 such that the light from the additional light source 402 overpowers the light from the excimer lamp 400. As yet another example, the at least one additional light source 402 may include a plurality of additional light sources that each output light having a different wavelength such that a combination of light from all additional light sources and the excimer lamp 400 appear white (or another desirable color).

In various embodiments, the at least one additional light source 402 may include an array of additional light sources.

Due to the elongated nature of the excimer lamp 400, the additional light sources 402 may be placed adjacent to each other along the X-axis such that they may extend along the length of the excimer lamp 400.

The system 302 may further include an elongated casing 404. The casing 404 may define a cavity in which the excimer lamp 400 and the at least one additional light source 402 are located. For example, the excimer lamp 400 and the at least one additional light source 402 may be mounted within the casing 404. The casing 404 may define an elongated outlet 406 through which a combination of the excimer light and the additional light exits the casing 404.

A first portion of the casing 404 may include a first reflector 408 on an inner surface thereof, and a second portion of the casing 404 may include a second reflector 410 on an inner surface thereof. The first reflector 408 may be designed to reflect the excimer light from the excimer lamp 400 and the additional light from the additional light source 402 towards the second reflector 410. In that regard, the first reflector 408 may have properties that facilitate reflection of light of all wavelengths that are generated by the excimer lamp 400 and the additional light source 402. For example, the first reflector 408 may be formed using polytetrafluoroethylene (PTFE) or any other reflective material. The shape of the first reflector 408 may be designed such that the light from the excimer lamp 400 and the additional light source 402 are directed towards a desirable point on the second reflector 410.

The second reflector 410 may be designed to reflect the excimer light from the excimer lamp 400 and the additional light from the additional light source 402 through the outlet 406 in a desirable orientation. In that regard, the second reflector 410 may have properties that facilitate reflection of light of all wavelengths that are generated by the excimer lamp 400 and the additional light source 402. For example, the second reflector 410 may be formed using PTFE. In that regard, the second reflector 410 may be formed with a PTFE coating 412. The PTFE coating 412 may have properties that diffuse the light from the excimer lamp 400 and the additional light sources 402 such that all light from the system 302 is blended together upon exit from the outlet 406. The shape of the second reflector 410 may be designed such that the light from the excimer lamp 400 and the additional light source 402 are directed out of the outlet 406 in a desirable direction. In that regard, the shape of the second reflector 410 may be significantly different than the shape of the first reflector 408.

Figures 5A, 5B, 5C:
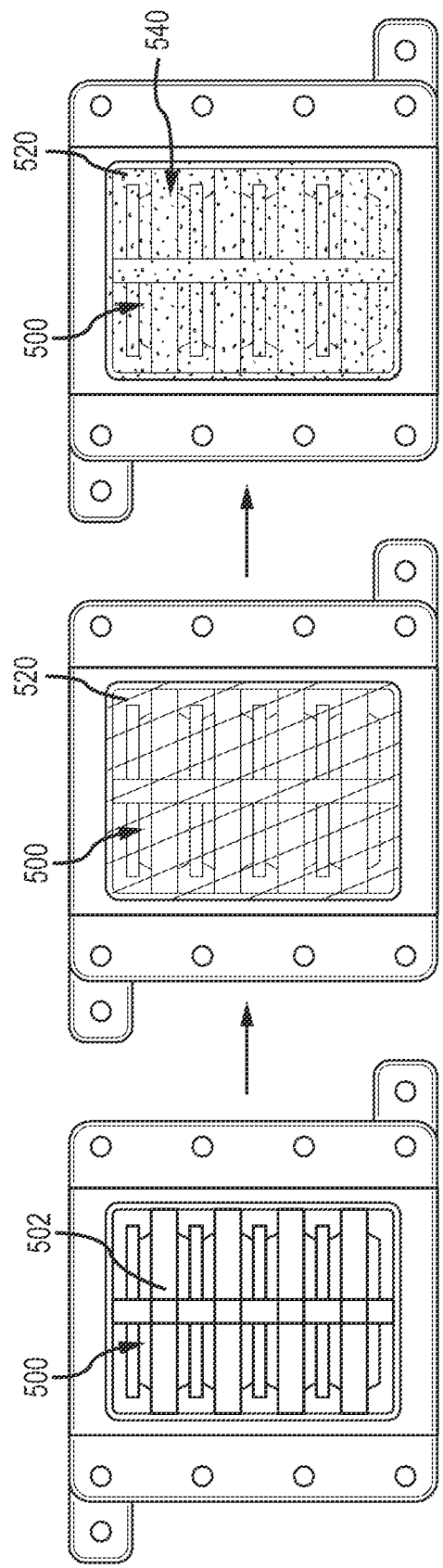
FIGS. 5A, 5B, and 5C illustrate an effect of various features of a system for improving an appearance of light from an excimer lamp, in accordance with various embodiments.

Turning to FIGS. 5A, 5B, and 5C, implementation of a system for improving an appearance of light from an excimer lamp is shown. FIG. 5A illustrates a plurality of excimer lamps 500 in a housing. The excimer lamps 500 each generate UV light and light having a visible wavelength or spectra. The visible light may undesirably appear as arcing.

FIG. 5B illustrates a cover 520 with a diffused pattern thereon located on the excimer lamps 500. As shown, the arcing is difficult to make out, but the visible light from the excimer lamps 500 still appears as an undesirable color.

FIG. 5C illustrates inclusion of an additional light source 540 (such as those described above) in addition to the cover 520. As shown, the light from the excimer lamps 500 and the additional light source 540, as viewed through the cover 520, appears as a soft white color.

Figure 7:
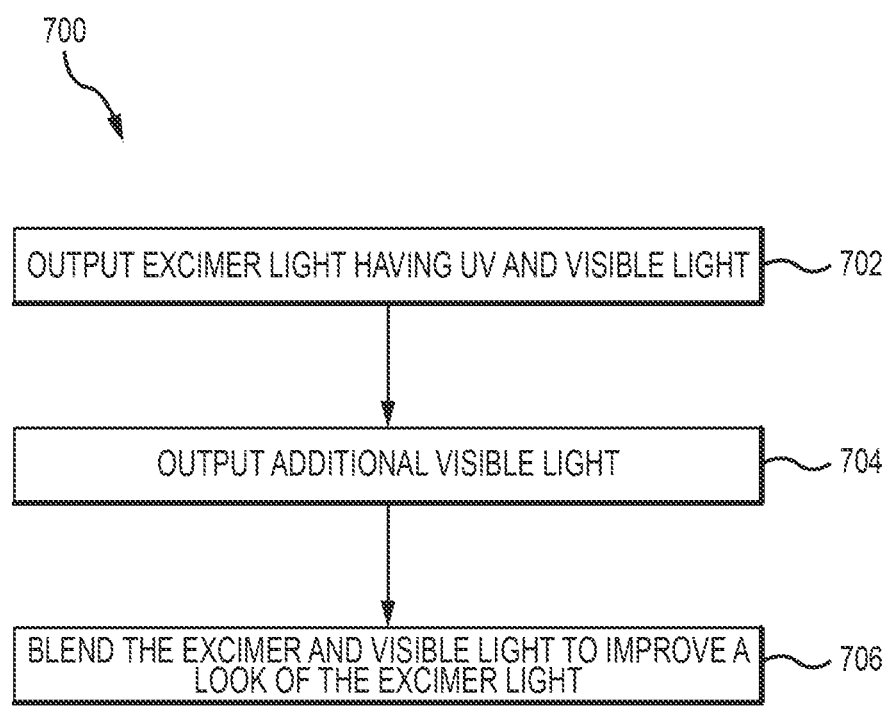
FIG. 7 is a flowchart illustrating a method for improving an appearance of light from an excimer lamp, in accordance with various embodiments.

Turning to FIG. 7, a method 700 for improving an appearance of light from an excimer lamp is shown. The method 700 may include, in block 702, outputting excimer light that includes UV light and visible light. The method 700 may further include outputting, by at least one additional light source, additional visible light. The additional visible light may have a single wavelength that mixes with the visible light from the excimer lamp to achieve a desired color, may include multiple wavelengths that mix to form a desirable color (e.g., blue and red wavelengths may be mixed to appear purple, or the like), or white or other colored light having a luminescence that is significantly greater than that of the visible light from the excimer lamp.

The method 700 further includes, in block 706, blending the excimer light and the visible light to improve a look of the excimer light. For example, the excimer lamp and the additional light source may be co-located in a casing such that the light blends together. As another example, a cover with an etched pattern may be positioned at an outlet of the casing. As yet another example, reflectors may be included in the casing to diffuse and reflect the light from the excimer lamp and the additional light source.

Where used in the context above, a controller may transmit power to a zone of a heating element in any of a number of manners. For example, the controller may directly output a current or voltage signal to the zone. As another example, the controller may control a switch to open or close to cease or begin, respectively, application of a current or voltage signal to the zone. As yet another example, the controller may control a voltage or current source to output or cease outputting the current or voltage signal to the zone. Any other method of direct or indirect application or control of application of a power signal (e.g., voltage or current signal) to the zone is contemplated by the present disclosure.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is intended to invoke 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for improving an appearance of light from an excimer lamp, the system comprising:
   the excimer lamp configured to output excimer light that includes ultraviolet light having an ultraviolet wavelength and visible light having a first visible wavelength or spectra;
   at least one additional light source configured to be packaged with the excimer lamp and to output additional light having a second visible wavelength or spectra; and
   a cover that is at least one of transparent or translucent to the ultraviolet wavelength and having a surface pattern that causes the excimer light to blend with the additional light.

2. The system of claim 1, wherein the ultraviolet wavelength of the ultraviolet light that is output by the excimer lamp is between 200 and 225 nanometers.

3. The system of claim 1, wherein the excimer lamp includes a plurality of excimer lamps spaced apart, and the at least one additional light source includes a plurality of additional light sources interspersed with the plurality of excimer lamps.

4. The system of claim 1, wherein a combination of the excimer light and the additional light appears white to a human eye.

5. The system of claim 1, wherein the second visible wavelength or spectra is selected to cause a combination of the visible light having the first visible wavelength or spectra and the additional light having the second visible wavelength or spectra to appear white to a human eye.

6. The system of claim 1, wherein the at least one additional light source includes at least two additional light sources that each output the additional light having a different visible wavelength such that a combination of the additional light that is output by the at least two additional light sources appears white to a human eye.

7. The system of claim 1, wherein a second luminescence of the additional light is at least one order of magnitude greater than a first luminesce of the visible light that is output by the excimer lamp so as to mask the visible light that is output by the excimer lamp.

8. The system of claim 1, wherein the cover includes a quartz glass.

9. The system of claim 8, wherein the quartz glass is etched to have the surface pattern.

10. A system for improving an appearance of light from an excimer lamp, the system comprising:
    the excimer lamp configured to output excimer light that includes ultraviolet light having an ultraviolet wavelength and visible light having a first visible wavelength or spectra;
    at least one additional light source configured to be packaged with the excimer lamp and to output additional light having a second visible wavelength or spectra;
    a casing having an outlet;
    a first reflector configured to reflect the excimer light and the additional light towards the outlet; and
    a second reflector configured to reflect the excimer light and the additional light from the first reflector, from the excimer lamp, and from the at least one additional light source out of the outlet, the second reflector configured to reflect the ultraviolet light.

11. The system of claim 10, wherein the second reflector has a polytetrafluoroethylene (PTFE) coating.

12. The system of claim 10, wherein the excimer lamp and the casing each have an elongated shape, and the at least one additional light source includes an array of light sources spaced along a length of the casing.

13. The system of claim 10, wherein the ultraviolet wavelength of the ultraviolet light that is output by the excimer lamp is between 200 and 225 nanometers.

14. The system of claim 10, wherein a combination of the excimer light and the additional light appears white to a human eye.

15. The system of claim 10, wherein the second visible wavelength or spectra is selected to cause a combination of the visible light having the first visible wavelength or spectra and the additional light having the second visible wavelength or spectra to appear white to a human eye.

16. The system of claim 10, wherein the at least one additional light source includes at least two additional light sources that each output the additional light having a different visible wavelength such that a combination of the additional light that is output by the at least two additional light sources appears white to a human eye.

17. The system of claim 10, wherein a second luminescence of the additional light is at least one order of magnitude greater than a first luminesce of the visible light that is output by the excimer lamp so as to mask the visible light that is output by the excimer lamp.

18. A method for improving an appearance of light from an excimer lamp, the method comprising:
    outputting, by the excimer lamp, excimer light that includes ultraviolet light having an ultraviolet wavelength and visible light having a first visible wavelength or spectra;
    outputting, by at least one additional light source, additional light having a second visible wavelength or spectra; and
    blending the excimer light with the additional light to hide the visible light having the first visible wavelength or spectra that is output by the excimer lamp.

19. The method of claim 18, wherein blending the excimer light with the additional light includes diffusing, by a quartz glass cover, the excimer light and the additional light.

20. The method of claim 18, wherein blending the excimer light with the additional light includes blending, using at least one reflector configured to reflect the excimer light, the excimer light and the additional light prior to a combination of the excimer light and the additional light leaving an outlet.

* * * * *